(12) United States Patent
Shirakawa et al.

(10) Patent No.: US 8,758,760 B2
(45) Date of Patent: Jun. 24, 2014

(54) ORAL VACCINE

(75) Inventors: Toshiro Shirakawa, Hyogo (JP); Masato Kawabata, Hyogo (JP); Tetsuo Takata, Hyogo (JP); Michiko Taniguchi, Hyogo (JP); Asako Okamoto, Hyogo (JP); Masanori Asada, Osaka (JP); Masaaki Nakatsuji, Osaka (JP)

(73) Assignee: Morishita Jintan Co., Ltd., Osaka (JP)

( * ) Notice: Subject to any disclaimer, the term of this patent is extended or adjusted under 35 U.S.C. 154(b) by 505 days.

(21) Appl. No.: 12/531,507

(22) PCT Filed: Mar. 19, 2008

(86) PCT No.: PCT/JP2008/055815
§ 371 (c)(1),
(2), (4) Date: Sep. 16, 2009

(87) PCT Pub. No.: WO2008/114889
PCT Pub. Date: Sep. 25, 2008

(65) Prior Publication Data
US 2011/0311617 A1    Dec. 22, 2011

(30) Foreign Application Priority Data

Mar. 19, 2007 (JP) .................................. 2007-70626

(51) Int. Cl.
*A61K 39/00* (2006.01)
*A61K 39/38* (2006.01)
*C12N 1/20* (2006.01)

(52) U.S. Cl.
USPC .................................. 424/184.1; 435/252.9

(58) Field of Classification Search
None
See application file for complete search history.

(56) References Cited

U.S. PATENT DOCUMENTS

| 4,481,157 A | 11/1984 | Morishita et al. |
| 5,478,570 A | 12/1995 | Sunohara et al. |
| 2006/0078618 A1* | 4/2006 | Constantinides et al. .... 424/489 |

FOREIGN PATENT DOCUMENTS

| JP | 61-151127 | 7/1986 |
| JP | 1398836 | 1/1987 |
| JP | 05-130876 | 5/1993 |
| JP | 07-069867 | 3/1995 |
| JP | 2999535 | 11/1999 |

OTHER PUBLICATIONS

Stubi et al J Travel Med 2000; 7:133-137.*
T. Takata et al.; "Genetically engineered *Bifidobacterium animalis* expressing the *Salmonella* flagellin gene for the mucosal immunication in a mouse model"; J Gene Med, 2006, vol. 8, No. 11, p. 1341-6.
Ch Simanjuntak et al.; "Oral immunisation against typhoid fever in Indonesia with Ty21a vaccine"; Lancet, 1991, vol. 338, No. 8774, p. 1055-9.
M.M. Levine et al.; "Duration of efficacy of Ty21a, attenuated *Salmonella typhi* live oral vaccine": Vaccine, 1999, vol. 17, Suppl 2, p. S22-7.
International Search Report, Application No. PCT/JP2008/055815, mailed May 27, 2008.
M. McClelland et al.; "Complete genome sequence of *Salmonella enterica* serovar Typhimurium LT2"; Nature, vol. 413, Oct. 2001, pp. 852-856.
J. Heidelberg et al.; "DNA sequence of both chromosomes of the cholera pathogen *Vibrio cholerae*"; Nature, vol. 406, Aug. 2000, pp. 477-484.
A. Tominaga et al.; "Characterization of cryptic flagellin genes in *Shigella boydii* and *Shigella dysenteriae*"; Genes Genet. Syst., vol. 76, 2001, pp. 111-120.
A. Takeuchi et al.; "Cloning and Expression in *Escherichia coli* of a Gene, hup, Encoding the Histone-like Protein HU of *Bifidobacterium longum*"; Biosci. Biotechnol. Biochem; vol. 66(3), 2002, pp. 598-603.

* cited by examiner

*Primary Examiner* — Gary B. Nickol
*Assistant Examiner* — Khatol Shahnan-Shah
(74) *Attorney, Agent, or Firm* — Renner, Otto, Boisselle & Sklar, LLP (57) ABSTRACT

The present invention provides an oral vaccine against a bacterial infectious disease (e.g., typhoid fever, cholera, or dysentery). The oral vaccine of the present invention is a capsule formulation in which a transformed microorganism that expresses a flagellin antigen protein or that secretes a flagellin antigen protein out of the cell of the microorganism is encapsulated with an acid-resistant membrane. Examples of the microorganism include intestinal bacteria belonging to the genus *Bifidobacterium*, the genus *Lactobacillus*, the genus *Lactococcus*, and the like. The form of the capsule formulation may be any one of a seamless capsule formulation, a soft capsule formulation, and a hard capsule formulation.

18 Claims, 2 Drawing Sheets

ORAL VACCINE

TECHNICAL FIELD

The present invention relates to an oral vaccine useful for preventing and treating a bacterial infectious disease, and a method for producing the same.

BACKGROUND ART

Typhoid fever is one of the infectious diseases caused by *Salmonella enterica* var. *Typhi*, which is a type of *salmonella* bacteria; infection being caused by the ingestion of contaminated drinking water, food, or the like. Typhoid fever is prevalent all over the world, particularly, in areas of Asia, Middle East, Eastern Europe, Africa, and Central and South America. Annually, 16 million people are affected by typhoid fever, and 0.6 million people die of this disease. Most of those killed are infants in developing countries. Currently, an attenuated *salmonella* bacterium (Ty21a) or the like is orally administered as a vaccine against typhoid fever caused by *salmonella* bacteria, but it cannot be administered to infants aged 5 or younger due to its side effects, such as diarrhea or vomiting. Once a person is affected by typhoid fever, an antibody against typhoid fever is developed inside the body, and immunity is acquired, but this effect does not last long.

Cholera is one of the infectious diseases caused by *Vibrio cholerae* O1 or O139. Cholera is prevalent all over the world, particularly, in Asia, Middle East, and Africa. Classical cholera epidemics repeatedly have occurred many times, and several million people have died of this disease due to its strong pathogenicity (death rate 20%). Currently, people are inoculated against this disease, but the effect of such inoculation is relatively low and said to be approximately 50%.

Bacterial dysentery (Shigellosis) is a bacterial infectious disease widely distributed throughout the world, and seen particularly in countries with poor hygiene. Bacterial dysentery is caused by intestinal bacteria belonging to the genus *Shigella*, which includes four groups consisting of *Shigella dysenteriae*, *S. flexneri*, *S. boydii*, and *S. sonnei*, in order of pathogenicity.

As described above, there are various bacterial infectious diseases, and it is clear that effective vaccines against bacterial infectious diseases are necessary. In particular, vaccines for preventing infectious diseases transmitted between humans are necessary. Currently, for example, some vaccines against various *salmonella* species are commercially available. These vaccines are sometimes effective, but have severe disadvantages. These vaccines typically induce antibodies as caused by infection with wild type bacteria, and an excessive load is placed on subjects.

In order to solve this problem, a study focused on the flagellum of bacteria has also been carried out. A flagellum is a long structure projecting from the cell surface of bacteria, and plays an important role when the cell moves and invades a host cell. The flagellum is comprised of a protein referred to as flagellin. This flagellin protein has been known to induce a high-level of antibodies. The antigenic protein flagellin of *Salmonella typhimurium* is described by McClelland M. et al. in *Nature*, vol. 413, p. 852 (2001). The antigenic protein flagellin of *Vibrio cholerae* is described by Heiderberg et al. in *Nature*, vol. 406, p. 477 (2000). Furthermore, the antigenic protein flagellin of *Shigella dysenteriae* is described by Tominaga A. et al. in *Genes Genet. Syst.*, vol. 76, p. 111 (2001). However, an effective vaccine using this sort of antibody against flagellum has not been provided yet.

DISCLOSURE OF INVENTION

It is an object of the present invention to provide means for using, as a vaccine, a flagellin protein derived from a bacterium that causes an infectious disease, because the infectious disease is not caused by the flagellin protein alone.

The present invention provides an oral vaccine against a bacterial infectious disease, in the form of a capsule formulation, comprising:
 a capsule membrane and
 a transformed microorganism that expresses a flagellin antigen protein,
 wherein the capsule membrane is acid resistant, and the transformed microorganism is encapsulated with the capsule membrane.

The present invention also provides a first method for producing an oral vaccine against a bacterial infectious disease, comprising the steps of:
 preparing a transformed microorganism that expresses a flagellin antigen protein; and
 enveloping the transformed microorganism in an acid-resistant capsule membrane, thereby producing an acid-resistant capsule formulation.

The present invention further provides a second method for producing an oral vaccine against a bacterial infectious disease, comprising the steps of:
 preparing a transformed microorganism that expresses a flagellin antigen protein;
 enveloping the transformed microorganism in a capsule membrane, thereby producing a capsule formulation; and
 providing the capsule membrane of the produced capsule formulation with acid resistance.

In one embodiment, the flagellin antigen protein is expressed in the cell of the microorganism.

In another embodiment, the flagellin antigen protein is secreted out of the cell of the microorganism.

In one embodiment, the microorganism is at least one selected from microorganisms belonging to the group consisting of the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella*.

In one embodiment, the oral vaccine is a vaccine against typhoid fever, cholera, or dysentery.

In one embodiment, the capsule formulation is a seamless capsule formulation, a soft capsule formulation, or a hard capsule formulation.

According to the present invention, a transformed microorganism that expresses an antigenic protein flagellin is contained in an acid-resistant capsule formulation. Therefore, the transformed microorganism is protected from gastric acid so as to allow it to be effectively delivered into the intestine alive. The formulation disintegrates in the intestine to release the transformed microorganism, which produces the antigenic protein flagellin. Flagellin itself is not infectious, however, an antibody is produced in the body. In particular, the transformed microorganism can be prepared from intestinal bacteria, as commonly referred to as good bacteria, such as bifidobacteria or lactic acid bacteria, which is viable in the intestine. Accordingly, the flagellin protein is produced in the intestine, and the produced flagellin protein is then regarded as an antigen so as to induce the production of antibody in the body. Thus, the infectious disease can be prevented.

Accordingly, the present invention can provide a method for preventing and treating bacterial infectious diseases with a small load of antibody.

BEST MODE FOR CARRYING OUT THE INVENTION

An oral vaccine against a bacterial infectious disease according to the present invention is in the form of a capsule formulation. Herein, a capsule contains contents therein is referred to as a "capsule formulation". The capsule formulation according to the present invention includes a capsule membrane and a transformed microorganism that expresses a flagellin antigen protein, wherein the capsule membrane is acid resistant. The capsule formulation including an acid-resistant capsule membrane and a transformed microorganism that expresses a flagellin antigen protein may have any configuration and any form as long as this capsule formulation has an acid-resistant capsule membrane and contains a transformed microorganism that expresses a flagellin antigen protein as the contents of the capsule, without excluding the formulation further including an additional constituent element. Accordingly, the transformed microorganism that expresses flagellin antigen protein is encapsulated with or enveloped in the acid-resistant capsule membrane (i.e., contained inside the capsule formed by the acid-resistant membrane). Herein, this capsule formulation is also referred to as an "acid-resistant capsule formulation".

Hereinafter, acquisition of a gene for flagellin (flagellin gene), preparation of a vector for expressing flagellin (flagellin expression vector), preparation of a transformed microorganism that expresses flagellin, and production of an acid-resistant capsule formulation containing the transformed microorganism for preparing an oral vaccine, and an oral vaccine against a bacterial infectious disease will be sequentially described at sections below.

1. Acquisition of Flagellin Gene

A gene that encodes flagellin is available based on known gene sequences. A gene that encodes flagellin can be acquired, for example, by performing amplification through a polymerase chain reaction (PCR) using genomic DNA or cDNA prepared from infectious pathogenic bacteria (e.g., bacterias causing *salmonella*, cholera, or dysentery) as a template with a pair of primers prepared based on the sequence information of the structural gene of the flagellin of the bacteria.

A gene that encodes typhoid fever flagellin is available based on the structural gene sequence of flagellin of *S. typhimurium* described by McClelland M. et al., in *Nature*, vol. 413, p. 852 (2001). For example, the gene can be acquired by performing amplification through a polymerase chain reaction (PCR) using chromosome DNA or cDNA of *S. typhimurium* as a template with the sequences of SEQ ID NOs: 1 and 2 as a pair of primers.

A gene that encodes cholera flagellin is available based on the structural gene of flagellin of *Vibrio cholerae* described by Heiderberg et al., in *Nature*, vol. 406, p. 477 (2000). For example, the gene can be acquired by performing amplification through PCR that uses chromosome DNA or cDNA of *V. cholerae* as a template with the sequences of SEQ ID NOs: 3 and 4 as a pair of primers.

A gene that encodes dysentery flagellin is available based on the structural gene of flagellin of *Shigella dysenteriae* described by Tominaga A. et al., in *Genes Genet. Syst.*, vol. 76, p. 111 (2001). For example, the gene can be acquired by performing amplification through PCR using chromosome DNA or cDNA of *S. dysenteriae* as a template, with the sequences of SEQ ID NOs: 5 and 6 in the sequence listing as a pair of primers.

2. Preparation of Flagellin Expression Vector

The flagellin gene prepared as in Section 1 above is incorporated into a plasmid to prepare an expression vector. There is no particular limitation on the plasmid used for preparing an expression vector, as long as the plasmid can effect the expression in intestinal bacteria. A plasmid derived from a microorganism belonging to the genus *Bifidobacterium* (e.g., pTB4, pTB6, pTB10, pBL67 or pBL78), a plasmid derived from a microorganism belonging to the genus *Streptococcus* (e.g., plasmid pC194), and the like are used. Furthermore, these plasmids can be complexed with an *Escherichia coli* plasmid (see Japanese Laid-Open Patent Publication No. 5-130876, for example).

In view of stable expression and ease of the preparation of DNA for preparing a transformed strain, a complex plasmid of a *Bifidobacterium longum* (*B. longum*) plasmid with an *Escherichia coli* plasmid is preferable among the above-described plasmids.

In view of selection for a transformed strain, the expression vector preferably has a selectable marker such as antibiotic resistance, auxotrophy, or the like.

The expression vector preferably has a control sequence for expressing or advantageously expressing flagellin. Examples of the control sequence include promoter sequences, leader sequences, propeptide sequences, enhancer sequences, signal sequences, terminator sequences, and the like. There is no particular limitation on the source of the control sequence, as long as it effects the expression in intestinal bacteria.

There is no particular limitation on the promoter sequence, as long as it effects the expression in intestinal bacteria. In view of efficient expression, a promoter sequence of a histone-like protein (HU) (hereinafter, may be referred to as an "HU promoter") of *B. longum* is preferably used. For example, an HU promoter gene can be obtained by amplifying and recovering the sequence from nucleotide positions 1 to 192 in the HU genes of SEQ ID NOs: 9 and 10 (*Biosci. Biotechnol. Biochem.* 66 (3), 598-603 (2002)), using chromosome DNA or cDNA of *B. longum* as a template with the sequences of SEQ ID NOs: 7 and 8 in the sequence listing as a pair of primers. For facilitating incorporation into a plasmid, an appropriate restriction enzyme site can be included in a primer sequence (HindIII for SEQ ID NO: 7, NcoI for SEQ ID NO: 8).

Furthermore, in view of improvement of expression efficiency, a terminator sequence is preferably included. As the terminator sequence, the terminator sequence of the HU gene is preferably used, which corresponds to a base sequence at positions 475 to 600 of SEQ ID NO: 9.

In addition to the above, a leader sequence, a propeptide sequence, an enhancer sequence, a signal sequence, and the like may be arranged as necessary. For example, it is preferable to contain a leader sequence and a signal sequence for secretion so that flagellin can be secreted out of the cell of the microorganism.

In this manner, control sequences, such as a promoter sequence and a terminator sequence, and a selectable marker gene are incorporated into the plasmid as necessary, to prepare a cloning vector. For example, a linker having a multicloning site is preferably arranged downstream of the promoter of the cloning vector. Using such a linker, a gene (DNA) that encodes flagellin is incorporated downstream of the promoter so that flagellin can be expressed in-frame.

Figure 1:
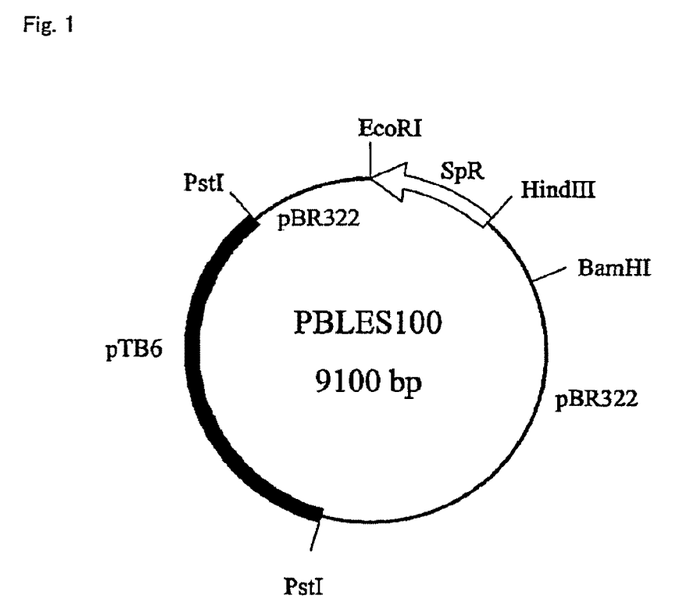
FIG. 1 is a schematic view showing the structure of plasmid pBLES100.

Examples of the plasmid for a cloning vector include pBLES100, pBLEM100, and the like. FIG. 1 shows a schematic view of the structure of pBLES100. The plasmid pBLES100 includes *Escherichia coli* vector pBR322-derived PstI-EcoRI fragment and PstI-HindIII fragment (total 4.4 kbp: line portion in FIG. 1), *B. longum* vector pTB6-derived PstI-PstI fragment (3.6 kbp: black band portion in FIG. 1), and a region that encodes *Enterococcus faecalis*-derived spectinomycin adenyltransferase (SpR) (1.1 kbp: outlined arrow in FIG. 1).

For example, a plasmid pBLES100 is prepared as follows. pTB6, which is a *B. longum*-derived plasmid, is cleaved with PstI, and inserted into the PstI site of *Escherichia coli* cloning vector pBR322 (manufactured by Takara Bio Inc.). Furthermore, a HindIII-EcoRI fragment region that encodes SpR of *Enterococcus faecalis* is inserted into the EcoRI-HindIII site of pBR322.

Figure 2:
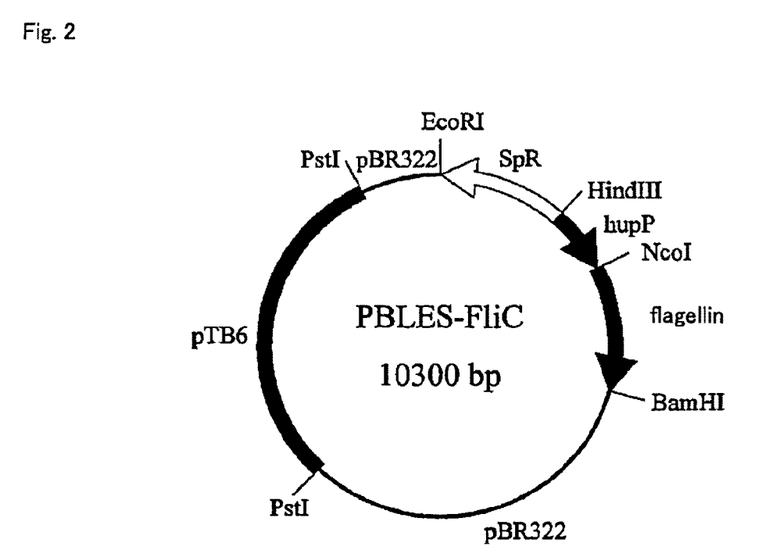
FIG. 2 is a schematic view showing the structure of pBLES-FliC prepared as a flagellin expression vector.

The acquired fragments for HU promoter sequence and flagellin gene (hereinafter, it may be referred to as a "FliC gene") are incorporated in-frame into this plasmid pBLES100 to prepare a vector that expresses flagellin. More specifically, the flagellin gene fragment is prepared by that PCR amplification is performed using the chromosome DNA of *S. typhimurium* as a template with the sequence of SEQ ID NO: 1 having the NcoI cleavage site and the sequence of SEQ ID NO: 2 having the BamHI cleavage site as a pair of primers, and the amplified fragment is cleaved with NcoI and BamHI. The HU promoter fragment is prepared by that PCR amplification is performed using the chromosome DNA of *B. longum* as a template with a primer of SEQ ID NO: 7 having the HindIII site and a primer of SEQ ID NO: 8 having the NcoI site as a pair of primers, and the amplified fragment is cleaved with HindIII and NcoI. These fragments are ligated to pBLES100 cleaved with HindIII and BamHI. Thus, a flagellin expression vector pBLES-FliC is obtained in which *salmonella* flagellin gene ("flagellin" in FIG. 2) is incorporated downstream of HU promoter gene ("hupP" in FIG. 2). FIG. 2 shows this expression vector pBLES-FliC. The thus obtained flagellin expression vector is used for transforming intestinal bacteria.

For secretory expression out of the cell of the microorganism, a vector may be used that is made by incorporating fragments for secretion signal peptide gene and for flagellin gene (FliC gene) in-frame into plasmid pBLES100. More specifically, the flagellin gene fragment is prepared by that PCR amplification is performed using chromosome DNA of *S. typhimurium* as a template with the sequence of SEQ ID NO: 1 having the NcoI cleavage site and the sequence of SEQ ID NO: 2 having the BamHI cleavage site as a pair of primers, and the amplified fragment is cleaved with NcoI and BamHI. The secretion signal peptide gene fragment is prepared by that PCR amplification is performed using chromosome DNA of *B. bifidum* as a template with a primer of SEQ ID NO: 11 having the HindIII site and a primer of SEQ ID NO: 12 having the NcoI site as a pair of primers, and the amplified fragment is cleaved with HindIII and NcoI. These fragments are combined with pBLES100 cleaved with BamHI and HindIII. Thus, a flagellin secretory expression vector pBLES-SP-FliC is obtained in which *salmonella* flagellin gene is incorporated downstream of the secretion signal peptide gene fragment. The thus obtained flagellin expression vector is used for transforming intestinal bacteria.

3. Preparation of Flagellin-Expressing Transformed Microorganism

There is no particular limitation on the host microorganism in which flagellin is to be expressed, as long as the bacterium is viable in the large intestine and the small intestine of human or animals (intestinal bacterium). When the host bacterium grows in the intestine, flagellin is expressed. The expressed flagellin exerts the antigenicity, by which an antibody is induced. Any bacteria viable in the intestine (i.e., intestinal bacteria), as commonly referred to as good bacteria, such as bifidobacteria or lactic acid bacteria can be favorably used.

Preferable examples of the microorganism include microorganisms belonging to the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella* (also collectively referred to as "lactic acid bacteria").

Examples of the microorganisms belonging to the genus *Bifidobacterium* (also collectively referred to as "bifidobacteria") include *Bifidobacterium adolescentis, B. angulatum, B. animalis* subsp. *animalis, B. animalis* subsp. *lactis, B. asteroides, B. bifidum, B. bourn, B. breve, B. catenulatum, B. choerinum, B. coryneforme, B. cuniculi, B. denticolens, B. dentium, B. gallicum, B. gallinarum, B. globosum, B. indicum, B. infantis, B. inopinatum, B. lactis, B. longum, B. magnum, B. merycicum, B. minimum, B. parvulorum, B. pseudocatenulatum, B. pseudolongum* subsp. *globosum, B. pseudolongum* subsp. *pseudolongum, B. pullorum, B. ruminale, B. ruminantium, B. saeculare, B. scardovii, B. subtile, B. suis, B. thermacidophilum*, and *B. thermophilum*.

Of these, *Bifidobacterium adolescentis, B. animalis* subsp. *animalis, B. animalis* subsp. *lactis, B. bifidum, B. breve, B. lactis, B. longum*, and *B. pseudolongum* subsp. *pseudolongum* are preferably used.

Examples of the microorganisms belonging to the genus *Lactobacillus* include *Lactobacillus acidophilus, L. amylovorus, L. animalis, L. brevis, L. brevis* subsp. *gravesensis, L. buchneri, L. bulgaricus, L. casei, L. casei* subsp. *casei, L. casei* subsp. *plantarum, L. casei* subsp. *tolerans, L. cellobiosus, L. curvatus, L. delbrueckii, L. delbrueckii* subsp. *bulgaricus, L. delbrueckii* subsp. *delbrueckii, L. delbrueckii* subsp. *lactis, L. divergens, L. fermentum, L. fructosus, L. gasseri, L. hilgardii, L. kefir, L. leichmannii, L. paracasei, L. paracasei* subsp. *paracasei, L. pentosus, L. plantarum, L. reuteri, L. rhamnosus, L. sakei, L. sakei* subsp. *sakei, L. sanfrancisco, L. vaccinostrcus*, and *Lactobacillus* sp.

Examples of the microorganisms belonging to the genus *Lactococcus* include *Lactococcus garvieae, L. lactis, L. lactis* subsp. *hordniae, L. lactis* subsp. *lactis, L. plantarum*, and *L. raffinolactis*.

Examples of the microorganisms belonging to the genus *Pediococcus* include *Pediococcus pentosaceus* and *P. acidilactici*.

Examples of the microorganisms belonging to the genus *Streptococcus* include *Streptococcus bovis, S. cremoris, S. faecalis, S. lactis, S. pyogenes*, and *S. thermophilus*.

Examples of the microorganisms belonging to the genus *Enterococcus* include *Enterococcus casseliflavus* and *E. faecalis*.

Examples of the microorganisms belonging to the genus *Leuconostoc* include *Leuconostoc citreum*, *Leuconostoc mesenteroides*, *L. mesenteroides* subsp. *mesenteroides*, and *L. mesenteroides* subsp. *dextranicum*.

Examples of the microorganisms belonging to the genus *Tetragenococcus* include *Tetragenococcus halophilus* and *T. muriaticus*.

Examples of the microorganisms belonging to the genus *Oenococcus* include *Oenococcus oeni*.

Examples of the microorganisms belonging to the genus *Weissella* include *Weissella viridescens*.

There is no particular limitation on the method for introducing a flagellin expression vector into intestinal bacteria, and methods commonly used by those skilled in the art may be used. Examples thereof include methods of electroporation; calcium phosphate; lipofection; using calcium ions; protoplast; and the like. Electroporation is preferably used. The electroporation can be performed at 0.5 to 20 kV/cm and 0.5 μsec to 10 msec, more preferably 2 to 10 kV/cm and 50 μsec to 5 msec.

A transformed strain is selected with a selectable marker contained in the flagellin expression vector. A medium for growing the transformed strain may be any medium suitable for the host microorganism. Examples of the medium include blood liver (BL) agar medium, de Man-Rogosa-Sharpe (MRS) agar medium, Gifu anaerobic medium (GAM) agar medium, improved GAM (TGAM) agar medium, Briggs agar medium, and yeast glucose peptone (YGP) agar medium. For selection pressure, antibiotics can be added to the medium, or amino acids can be deleting from or adding to the medium, depending on the selectable marker.

The expression of flagellin in a transformed microorganism can be confirmed, for example, using the Western blotting. The expression of flagellin can be confirmed by that: First, the transformed microorganism is lysed, for example, using a non-ionic surfactant, including polyoxyethylene sorbitan ester (Tween (registered trademark) 20, 40, 60, 65, 80, 85), and sorbitan ester (Span (registered trademark) 20, 40, 60, 65, 80, 85), and the like; then diluted with phosphate buffer, citrate buffer, borate buffer, tris(hydroxymethyl)aminomethane(Tris)-hydrochloride buffer, or the like; then subjected to electrophoresis with sodium dodecyl sulfate-polyacrylamide gel (SDS-PAGE), tris-glycine-polyacrylamide gel, or the like; then transferred to nitrocellulose membrane, polyvinylidene fluoride (PVF) membrane, or the like; and then reacted with an antibody (immunoglobulin G (IgG)) against flagellin, and further reacted with a secondary antibody with a fluorescent label. For secretory expression of flagellin by a transformed microorganism, it can be confirmed by that subsequent to the selection for the transformed strain, a supernatant is obtained through centrifugal separation and subjected to Western blotting as described above.

The transformed microorganism in which expression of flagellin has been confirmed may be cultured, recovered, and used directly for the production of a formulation, using any methods commonly used by those skilled in the art. Alternatively, the transformed microorganism may be used in a dry form. The transformed microorganism can be dried by the treatment in which a low-temperature treatment such as freeze drying or low-temperature drying is performed so that the microorganism can grow when exposed to growth conditions such as those in an intestinal environment or a medium.

4. Production of an Acid-Resistant Capsule Formulation Containing the Transformed Microorganism In order to allow the transformed microorganism that expresses a flagellin protein to act as an oral vaccine, the transformed microorganism has to pass through the stomach, reach the intestine, and grow therein. However, mostly orally ingested intestinal bacteria, such as lactic acid bacteria, die due to significantly low pH in the stomach, the pH of 1 to 3. Typically, it is said that the ratio of intestinal bacteria reaching the intestine while maintaining their ability to proliferate is one 10000th or less of the amount of bacteria administered. Accordingly, in order to use the transformed microorganism according to the present invention, it is necessary to prevent the transformed microorganism from being affected by gastric acid so that the transformed microorganism can reach the human intestine alive and grow in the intestine to express flagellin.

Thus, the present invention provide a capsule formulation in which the transformed microorganism is encapsulated with or enveloped in an acid-resistant capsule membrane, on the other word, the pharmaceutical is in the form of a capsule formulation in which the transformed microorganism is contained within a capsule having an acid-resistant membrane. There is no particular limitation on the configuration, the shape, or the like of the capsule formulation, as long as the membrane is resistant to gastric-acid. Specifically, the configuration is desirable that prevents gastric acid from penetrating the capsule and contacting the transformed microorganism. The capsule membrane may be an insoluble membrane at a pH of 4 or lower, preferably at a pH of 1 to 3. There is no particular limitation on the method for encapsulation.

Seamless Capsule Formulation

The capsule for providing with resistance to gastric acid may be preferably in the form of a seamless capsule. Herein, "seamless capsule" refers to a type of soft capsule in which the contents are enveloped in a seamless membrane. The seamless capsule can have a multi-layered structure consisting of two or more layers, and preferably has a multi-layered structure consisting of three or more layers. Typically, an innermost layer can contain the contents (being the transformed microorganism in the case of the present invention), and an outer layer (or the outermost layer) can act as the membrane. Specifically, the transformed microorganism is encapsulated with the membrane.

Figure 3:
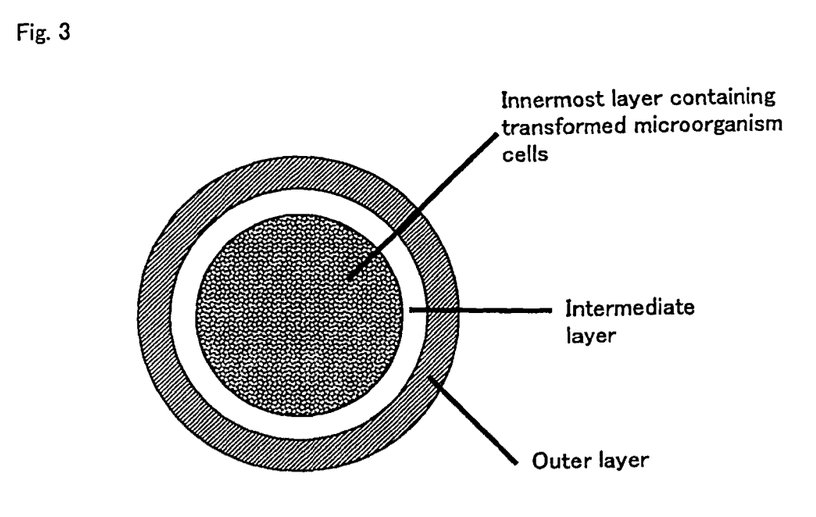
FIG. 3 is a schematic cross-sectional view showing the configuration of a seamless capsule formulation of three layers containing a flagellin-expressing transformed microorganism.

Hereinafter, preparation of a three-layered seamless capsule formulation will be described. FIG. 3 is a schematic cross-sectional view of a three-layered seamless capsule formulation. This three-layered structure consists of an innermost layer, an intermediate layer that covers the innermost layer, and an outer layer that covers the intermediate layer.

The innermost layer includes the transformed microorganism and a non-aqueous solvent or solid component for suspending or mixing the transformed microorganism (hereinafter, which component is referred to as an "innermost layer substance"). There is no particular limitation on the innermost layer substance. Examples thereof include various fat and oils, fatty acids, fatty acid esters of sugars, aliphatic hydrocarbons, aromatic hydrocarbons, linear ethers, higher fatty acid esters, higher alcohols, and terpenes. Specific examples thereof include, but are not limited to, soybean oil, sesame oil, palm oil, palm kernel oil, corn oil, cottonseed oil, coconut oil, rapeseed oil, cacao butter, beef tallow, lard, horse oil, whale oil, hydrogenated fat and oils of these natural fat and oils having a melting point of 40° C. or lower, margarine, shortening, glycerin fatty acid esters, sucrose fatty acid esters, camphor oil, peppermint oil, α-pinene, D-limonene, and the like. These innermost layer substances can be used alone or in a combination of two or more.

A material used for the intermediate layer is, among the above-listed innermost layer substances, a material having a melting point of 20° C. to 50° C. and different from the innermost layer substance, more preferably a material which is in solid state at ambient temperatures. As, in the examples set forth below, hydrogenated palm kernel oil having a melting point of 34° C. and hydrogenated palm kernel oil having a melting point of 43° C. are used as the innermost layer substance and the inner layer material, respectively, the same species of fat and oils may be used as the innermost layer substance and the inner layer material, that are subjected to hydrogenation so as to have different melting points. This intermediate layer can act as preventing the permeation of water and oxygen and preventing contact with gastric acid. The material to be selected may be determined in consideration of the storage period of the capsule and the like.

A material used for the outer layer (being the outermost layer in the case of a structure having three or more layers) may be a mixture of a protein and a water-soluble polyhydric alcohol; a mixture of a protein, a water-soluble polyhydric alcohol, and a polysaccharide; a mixture of a polysaccharide and a water-soluble polyhydric alcohol; or the like. Examples of the protein include gelatin and collagen. Examples of the water-soluble polyhydric alcohol include sorbitol, mannitol, glycerin, propylene glycol, and polyethylene glycol. Examples of the polysaccharide include agar, gellan gum, xanthan gum, locust bean gum, pectin, alginate, carrageenan, gum arabic, dextrin, modified dextrin, starch, modified starch, pullulan, pectin, and carboxymethylcellulose salt. In the case where pectin, alginate, gellan gum, or carrageenan is used, an alkali metal salt or an alkaline-earth metal salt may be added as appropriate.

The three-layered seamless capsule formulation is prepared using any techniques known by those skilled in the art, such as the dropping method using a triple nozzle described in Japanese Patent No. 1398836. In this dropping method, the innermost layer substance combined with the transformed microorganism (e.g., the freeze-dried cells of the microorganism), which is preferably a suspension of the transformed microorganism (preferably, the freeze-dried cells of the microorganism) in a hydrophobic solvent material that is non-fluid at 20 to 50° C., from the innermost nozzle of the concentric triple nozzle, a material forming the intermediate layer (e.g., a liquid obtained by melting a material in the form of a solid at room temperature) from the intermediate nozzle, and a solution of a material forming the outer layer (membrane) from the outermost nozzle are simultaneously ejected, and dropped into a carrier liquid (e.g., corn oil, rapeseed oil, or the like) which flows under cooling down, thereby forming a three-layered "seamless" capsule in which the transformed microorganism is contained in the innermost layer. Accordingly, the transformed microorganism is encapsulated with or enveloped in the seamless membrane.

The thus formed capsule is then dried. For example, the drying is performed by ventilation at ambient temperatures. Typically, the capsule is dried, for example, in the air at 5° C. to 30° C. The drying time is preferably 2 to 12 hours. As described in Japanese Laid-Open Patent Publication No. 07-069867, a capsule that has been ordinarily dried as described above may be preferably further subjected to vacuum drying or vacuum freeze drying. The degree of vacuum can be kept at 0.5 to 0.02 torr. The capsule can be frozen and dried at −20° C. or lower in the case of vacuum freeze drying. There is no particular limitation on the time for vacuum drying or vacuum freeze drying, but it is typically 5 to 60 hours, preferably 24 to 48 hours. If the time is shorter than 5 hours, drying is insufficient and water present in the capsule may negatively affect the contents.

In the case of a capsule obtained using the method as described in Japanese Laid-Open Patent Publication No. 07-069867, water is sufficiently removed from the capsule by vacuum freeze drying, and, thus, the Aw value can be 0.20 or less, and the heat conductivity can be 0.16 kcal/mh° C. or less. By vacuum drying or vacuum freeze drying, the amount of water is naturally reduced while the capsule is sufficiently dried and becomes porous. Thus, the heat conductivity is significantly lower than that in the case where ordinary drying is simply performed.

The Aw value refers not to an absolute content of water present in the sample, but to a value determined by the state in which water is present, that is, the degrees of freedom for water in the sample. The Aw value is an indicator indicating water that can directly affect chemical reaction or microorganism growth, and is measured using an electrical-resistance-type water activity measuring method (e.g., Aw meter WA-360, Shibaura Electronics Co., Ltd.). The heat conductivity is measured using the Fitch method or the like. The Aw value is preferably 0.20 or less, and the heat conductivity is preferably 0.02 to 0.08 kcal/mh° C.

In order to provide the capsule membrane of the seamless capsule formulation with acid resistance, an acid resistant outer layer is formed, or the membrane (the outermost layer) of the prepared seamless capsule is treated so as to be acid resistant.

Examples of the method for forming an acid-resistant outer layer include addition of pectin, alginate, gum arabic, or the like in an amount of 0.01 to 20 wt %, preferably 0.1 to 10 wt % to gelatin, agar, carrageenan, or the like, which has a gelling ability.

Examples of the method for providing the membrane (the outermost layer) of the prepared seamless capsule with acid resistant include crosslinking of the outer layer (the outermost layer) of the seamless capsule and coating of the surface of the seamless capsule, which may be performed alone or in combination.

For crosslinking of the outer layer which contains a protein, the seamless capsule is first prepared, and then sufficiently washed with water, and then, the water-washed seamless capsule is added to an aqueous solution containing a crosslinking agent. Thus, the surface of the outer layer is subjected to a crosslinking treatment. As the crosslinking agent, conventionally known crosslinking agents may be used. Examples of the crosslinking agent include formaldehyde, acetaldehyde, propionaldehyde, glyoxal, glutaraldehyde, cinnamaldehyde, vanillyl aldehyde, acetone, ethyl methyl ketone, ethylene oxide, propylene oxide, potassium alum, and ammonium alum. Typically, the outer layer is treated by adding 1 part by weight of seamless capsule to 50 to 100 parts by weight of aqueous solution containing 0.1 to 2 w/v %, preferably 0.5 to 2 w/v %, of a crosslinking agent, and agitating the mixture for 10 to 300 seconds. Here, the amount of crosslinking agent used and the period of time for action vary depending on the type of the crosslinking agent. After the surface of the outer membrane is subjected to the crosslinking treatment, the outer membrane is washed sufficiently with water to remove the aqueous solution containing the crosslinking agent, and water in the outer layer is dried out.

For the crosslinking of the protein-containing outer layer, the crosslinking may be performed through enzymatic treatment with transglutaminase. In this case, the outer layer is treated by adding 1 part by weight of produced seamless capsule to 50 to 100 parts by weight of aqueous solution containing 0.1 to 10 w/v %, preferably 0.5 to 2 w/v %, of enzyme, and agitating the mixture for 1 to 300 minutes. The resultant is washed with water and dried as described above.

For the coating, after the produced wet seamless capsule is dried, the seamless capsule is conventionally coated with shellac, ethylcellulose, hydroxypropylmethylcellulose, hydroxypropylcellulose, polyvinylpyrrolidone, cellulose TC-5, vinylpyrrolidone-vinyl acetate copolymer, zein, ethylene wax, or the like as the base material, and castor oil, rapeseed oil, dibutylphthalate, polyethylene glycol, glycerin, stearic acid, fatty acid ester, sorbitan palmitate, polyoxyethylene stearate, acetylated monoglyceride, or the like as the plasticizer.

The capsule membrane can be further provided with entericity. Thereby, the capsule is protected from an acidic solution and the like (such as gastric acid) in the stomach, and disintegrates in the intestine so that the transformed microorganism is released from the inside of the capsule to sufficiently effect the production of antigen in the intestine. The capsule membrane can be provided with entericity by producing an enteric capsule as commonly practiced by those skilled in the art. A mixture of gelatin and pectin can be used as the outer layer material of the seamless capsule to make the membrane enteric. The acid-resistant outer layer is further provided with entericity by preparing through addition of pectin, alginate, gum arabic, or the like in an amount of 0.01 to 20 wt %, preferably 0.1 to 10 wt % to gelatin, agar, carrageenan, or the like, which has a gelling ability.

The seamless capsule formulation may be in the shape of a sphere due to the production method. The average particle size of the seamless capsule is 0.3 to 10 mm, preferably 1.5 to 8.0 mm.

The thus obtained seamless capsule formulation can be stored for six months or more while maintaining the activity of the transformed microorganism at room temperature. If the formulation is stored at 10° C. or lower, extended storage for one year or more is possible.

Soft Capsule Formulation

As in the case of the seamless capsule formulation, a soft capsule formulation can be the encapusulation of a suspension of the transformed microorganism in a non-aqueous solvent (as capsule contents) with a membrane sheet. The material of the membrane sheet is as mentioned for the outer layer of the seamless capsule.

A soft capsule formulation can be prepared using any known procedures, for example, as described in Japanese Patent No. 2999535. For example, using a rotary die, while the contents are injected and filled, the membrane sheet is heated through the die, so as to envelop and encapusulate the contents. For the action of releasing the transformed microorganism in the intestine, an oil, which is a release agent, is removed from the resultant soft capsule through washing with a polar solvent (e.g., methanol, ethanol, propanol, or isopropanol). Subsequently, the capsule can be made acid resistant by performing the crosslinking treatment and the coating treatment in combination, or performing either one of the treatments, as in the case of the seamless capsule.

The acid-resistant membrane sheet can be also prepared based on any known methods such as through addition of pectin, alginate, gum arabic, or the like in an amount of 0.01 to 20 wt %, preferably 0.1 to 10 wt % to gelatin, agar, carrageenan, or the like, which has a gelling ability. Alternatively, the membrane sheet can be made acid resistant, by performing the crosslinking treatment and the coating treatment in combination, or performing either one of the treatments. The thus obtained acid-resistant membrane sheet can be used to produce a soft capsule formulation in which the transformed microorganism is encapsulated with the acid-resistant membrane. For example, from the obtained acid-resistant membrane sheet a capsule is shaped, the contents are introduced into the capsule, and then a seam of the capsule is melted and joined so as to envelop the contents, using known techniques.

The soft capsule formulation may be in the shape of a sphere, an ellipse, or a rectangle. The soft capsule preferably has a major axis of 3 to 16 mm and a minor axis of 2 to 10 mm, and more preferably has a major axis of 5 to 7 mm and a minor axis of 2 to 3 mm.

The thus obtained soft capsule formulation can be stored for six months or more while maintaining the activity of the transformed microorganism at room temperature. If the formulation is stored at 10° C. or lower, extended storage for one year or more is possible.

Hard Capsule Formulation

A hard capsule formulation can be produced by molding a capsule membrane into a body and a cap in advance, filling the body of capsule with contents, and combining the resultant with the cap of capsule.

Examples of the material of the membrane of the hard capsule formulation include gelatin, cellulose, pullulan, carrageenan, and cellulose derivatives such as hydroxypropylmethylcellulose. The hard capsule can be molded using any methods commonly used by those skilled in the art. The molded capsule may be commercially available capsules. The contents can be encompassed with and enveloped in the membrane.

The contents may be a mixture obtained by sufficiently mixing the transformed microorganism with a vehicle (e.g., silicic anhydride, synthetic aluminum silicate, lactose, cornstarch, or crystalline cellulose), or powders containing dried powders of the transformed microorganism.

After the contents are contained in the capsule, the membrane of the capsule may be coated. For this coating, the materials and the methods as mentioned for the outer layer of the seamless capsule can be applied to provide the membrane with acid resistance and preferably disintegrativity in the intestine (entericity). This coating also allows the capsule membrane to seal so as to encapsulate the contents.

The acid-resistant membrane sheet can be also prepared based on any known methods such as through addition of pectin, alginate, gum arabic, or the like in an amount of 0.01 to 20 wt %, preferably 0.1 to 10 wt % to gelatin, agar, carrageenan, or the like, which has a gelling ability. Alternatively, the membrane sheet can be made acid resistant, by performing the crosslinking treatment and the coating treatment in combination, or performing either one of the treatments. The thus obtained acid-resistant membrane sheet can be used to produce a hard capsule formulation in which the transformed microorganism is encapsulated by the acid-resistant membrane. For example, from the obtained acid-resistant membrane sheet a hard capsule is shaped, the contents are introduced into the shaped hard capsule, and then a seam of the capsule is melted and joined so as to envelop the contents, using a known technique.

The thus obtained hard capsule formulation can be stored for six months or more while maintaining the activity of the transformed microorganism at room temperature. If the formulation is stored at 10° C. or lower, extended storage for one year or more is possible.

5. Oral Vaccine Against a Bacterial Infectious Disease

After oral administration, the acid-resistant capsule formulation (the seamless capsule formulation, the soft capsule formulation, and the hard capsule formulation) obtained as explained in Section 4 described above passes through the stomach having a pH of 1 to 3, reaches the intestine, and then disintegrates in the intestine. The transformed microorganism is released through the disintegration of the formulation, grows, produces, and preferably secretes flagellin out of the cell of the microorganism in an intestinal environment. The flagellin is then recognized as an antigen to produce an antibody. Accordingly, the acid-resistant capsule formulation can be an effective oral vaccine against a microorganism having flagellin.

EXAMPLES

Hereinafter, the present invention will be described by way of examples, but the present invention is not limited to these examples.

Example 1

Preparation of Acid-Resistant Capsule Formulation Containing Bifidobacteria Producing Typhoid Fever Antigen A. Amplification of *S. Typhimurium* Flagellin Gene Through PCR

*S. typhimurium* ATCC 14028 was cultured in LB medium (manufactured by Invitrogen) at 37° C. for 12 hours. After completion of the culture, the genomic DNA was conventionally extracted from *S. typhimurium*. The extracted genomic DNA was amplified using a kit for PCR reaction (manufactured by Applied Biosystems) with Ampli Taq DNA polymerase (0.5 units) according to the instruction. As a pair of primers, the following were used: SEQ ID NO: 1 (forward): 5'-CATGCCATGGATGGCACAGTCATTAATACA-3' (CCATGG at positions 5 to 10 is the NcoI cleavage site), and SEQ ID NO: 2 (reverse): 5'-CGCGGATCCTTAACGCAG-TAAAGAGAGGAC-3' (GATCCT at positions 5 to 10 is the BamHI cleavage site). PCR was performed using 40 μL of reaction liquid containing 125 ng of template DNA, 0.5 μmol of each primer, 2.5 units of Pfu DNA polymerase, 4 μL of ×10 buffer solution for Pfu DNA polymerase, and 200 μmol of each dNTP, under 30 cycles of at 94° C. for 1 minute, at 55° C. for 1 minute, and at 72° C. for 1 minute, and then at 72° C. for 10 minutes. After completion of PCR, the resultant was cleaved with NcoI and BamHI. Thus, the fragment for flagellin gene was prepared.

B. Amplification of HU Promoter Through PCR

*B. longum* ATCC 15703 strain was cultured in MRS medium (manufactured by Nippon Becton Dickinson Company, Ltd.) at 37° C. for 12 hours. After completion of the culture, the genomic DNA was conventionally extracted from *B. longum*. PCR was performed as in Section A described above. As a pair of primers, the following were used: SEQ ID NO: 7 (forward): 5'-CGCCAAGCTTTGGGCGCGGCGGC-CATGAAG-3' (AAGCTT at positions 5 to 10 is the HindIII cleavage site), and SEQ ID NO: 8 (reverse): 5'-CGCGC-CATGGAAAGCATCCTTCTTGGGTCA-3' (CCATGG at positions 5 to 10 is the NcoI cleavage site). After completion of PCR, the resultant was cleaved with HindIII and NcoI. Thus, the fragment for HU promoter gene was prepared.

C. Preparation of Expression Vector

The plasmid pBLES 100 was cleaved with BamHI and HindIII, and combined with and ligated to the *salmonella* flagellin gene fragment prepared in Section A described above and the HU promoter gene fragment prepared in Section B described above. Thus, an expression vector pBLES-FliC was obtained.

D. Introduction of Expression Vector into *B. Animalis*

*B. animalis* ATCC 27536 was inoculated into MRS medium, and grown to the mid-logarithmic growth phase by still standing at 37° C. for 12 hours under the atmosphere of nitrogen containing 10% carbon dioxide. The resultant culture was centrifuged, and the cells of the microorganism were collected and washed three times with PBS (obtained by diluting 8 g of sodium chloride, 0.2 g of potassium chloride, 1.44 g of disodium hydrogen phosphate, and 0.24 g of potassium dihydrogen phosphate with 1 L of distilled water, and adjusting the pH to 7.4). Then, PBS was added to $5 \times 10^8$ cells/mL so as to obtain a suspension of *B. animalis*. Then, 5 μg DNA/5 μL) of pBLES-FliC prepared in Section C described above was added to 50 μL of this suspension, and the resultant was placed in a 0.2 cm-wide electroporation cuvette and treated under the conditions of 5 μs, 1000 V for transformation.

The culture was performed in a spectinomycin (50 μg/ml)-containing BL agar medium (manufactured by Nissui Pharmaceutical Co., Ltd) at 37° C. under the atmosphere of nitrogen containing 10% carbon dioxide. Thus, transformed *B. animalis* was obtained.

E. Western Blotting

Whether or not the transformed *B. animalis* expresses a flagellin protein was confirmed as follows. *B. animalis* was diluted with a phosphate buffer (pH 6.8) containing 1 w/v % Tween (registered trademark) 80 and a buffer solution A (126 mM Tris hydrochloride, 20 w/v % glycerin, 4 w/v % sodium dodecyl sulfate, 1.0 w/v % 2-mercaptoethanol, 0.05 w/v % bromophenol blue, pH 6.8). Then, 5 μg of the resultant was subjected to electrophoresis (tris-glycine polyacrylamide gel), and then subjected to electroblotting to transfer resolved proteins to a nitrocellulose membrane, and then subjected to ELISA with IgG1 (manufactured by ViroStat) specific to flagellin common to *salmonella* species and horseradish peroxidase (HRP)-labelled secondary antibody (1:500). Thus, the expression of flagellin was confirmed.

F. Preparation of Freeze-Dried Microorganism Powder of the Transformed Microorganism First, 2 platinum loops of the transformed *B. animalis* were inoculated into 1 L of MRS medium (manufactured by Nippon Becton Dickinson Company, Ltd.) containing 50 μM of spectinomycin, and cultured at 37° C. for 18 hours with the injection of gas of nitrogen containing 10% carbon dioxide. The pH was adjusted to 5.5 with 10M sodium hydroxide aqueous solution by an automatic pH adjuster to avoid the decrease of pH during the culture. After the culture for 15 hours, the cells were appropriately diluted with an anaerobic diluent, applied to BL agar medium containing 50 μM of spectinomycin, and counted for the viable cell number of colonies. Here, the anaerobic diluent was obtained by dissolving 6.0 g of disodium hydrogen phosphate, 4.5 g of potassium dihydrogen phosphate, 0.5 g of L-cysteine monohydrochloride, 0.5 g of Tween (registered trademark) 80, and 1.0 g of agar in 1 L of distilled water, and steam-sterilizing the resultant at 121° C. for 15 minutes.

After culture, the cells were collected by centrifugal separation (15000×g, 20 minutes), and to the cells, 120 g of distilled water, 12 g of sodium citrate, and 8 g of sodium malate were added to obtain a suspension of the cells. Then, 8 g of Avicel FD-101 (manufactured by Asahi Kasei Corporation) was added to this suspension, and the resultant was sufficiently agitated, frozen, and then dried in a vaccume. Subsequently, dextrin was added in an amount twice as much as the obtained powders. Thus, freeze-dried microorganism cell powders were obtained.

G. Preparation of Acid-Resistant Seamless Capsule Formulation

As described below, the acid-resistant seamless capsule formulation containing the transformed microorganism cells was prepared using a capsule-producing apparatus provided with a coaxial triple nozzle.

First, 400 g of hardened oil (hydrogenated palm kernel oil having a melting point of 34° C.) was melted, and 100 g of the freeze-dried microorganism cell powders obtained in Section F described above was then dispersed therein. This dispersion from the innermost nozzle of the concentric triple nozzle, a molten hardened oil (hydrogenated palm kernel oil having a melting point of 43° C.) from the intermediate nozzle positioned on the outer side of the innermost nozzle, and a gelatin solution (obtained by dissolving 600 g of gelatin, 300 g of glycerin, and 100 g of pectin in 4 kg of purified water) from the outermost nozzle were simultaneously ejected, and dripped into rapeseed oil which flows under cooling at 15° C., thereby forming a formulation in which the transformed microorganism cells were encapsulated in a three-layered seamless capsule having a diameter of 2.5 mm. This capsule formulation was dried by ventilation at 20° C. for 10 hours, and then dried in a vacuum at room temperature. Thus, the water activity Aw value was reduced to 0.20 or less and the heat conductivity was reduced to 0.16 kcal/mh° C. or less in the capsule.

H. Preparation of Acid-Resistant Soft Capsule Formulation

First, 50 g of freeze-dried microorganism cell powders obtained in Section F described above were suspended in 300 g of rapeseed oil to prepare a fluid content of a soft capsule. Then, 400 g of gelatin and 100 g of glycerin were added to 200 g of distilled water, agitated at 60° C., and dissolved, and the resultant was shaped into a sheet, thereby obtaining a gelatin membrane, which was used as the membrane of the soft capsule. The gelatin membranes were send to a space between a pair of rotating cylindrical dies, and the fluid content was ejected to a space between the gelatin membranes by a pump moving in conjunction with the dies, thereby forming the encapsulation.

Then, 400 g of the encapsulations were placed in a rolling granulator, and a solution obtained by dissolving 10 g of shellac and 1 g of castor oil in 400 g of methanol-ethyl acetate mixed liquor (1:1, v/v) was sprayed onto the entire surface of the soft capsules to a coating membrane thickness of 0.3 mm. Thus, it was obtained that 400 g of soft capsule formulations having a major axis of 4 mm and a minor axis of 3 mm, encapsulating the transformed microorganism cells, and having an acid-resistant coating.

I. Preparation of Acid-Resistant Hard Capsule Formulation

The freeze-dried microorganism cell powders obtained in Section F described above were used as the contents of a hard capsule. For the hard capsule membrane, a commercially available capsule of No. 5 as defined in Japanese Pharmacopoeia was used. The contents were filled with the body of capsule, and combined with the cap of capsule, thereby forming the encapsulation.

Then, 100 g of the encapsulations were placed in a rolling granulator, and a solution obtained by dissolving 10 g of shellac and 1 g of castor oil in 400 g of methanol-ethyl acetate mixed liquor (1:1, v/v) was sprayed onto the entire surface of the hard capsules to a coating membrane thickness of 0.3 mm. Thus, 100 g of hard capsule formulations encapsulating the transformed microorganism cells and having an acid-resistant coating were obtained.

Example 2

Preparation of Acid-Resistant Capsule Formulation Containing Lactic Acid Bacteria Producing Cholera Antigen

*V. cholerae* ATCC 11628, which produces a cholera antigen, was cultured in LB medium at 37° C. for 12 hours. After completion of the culture, the genomic DNA was conventionally extracted from *V. cholerae*. PCR was performed as in Example 1, using the extracted genomic DNA as a template with the sequences of SEQ ID NO: 3 (forward) and SEQ ID NO: 4 (reverse) as a pair of primers. The resultant amplified fragment was recovered and cleaved with NcoI and BamHI. Thus, the fragment for cholera flagellin gene was prepared. The pBLES-FliC prepared in Example 1 was digested with NcoI and BamHI, and a large fragment was recovered. This fragment and the cholera flagellin gene fragment were ligated to each other. Thus, a cholera antigen-expressing expression vector pBLES-Vc was obtained.

The obtained cholera flagellin expression vector pBLES-Vc was used to transform *Lb. plantarum* ATCC BAA-793 to prepare *Lb. plantarum* producing a cholera antigen. The expression of the cholera antigen was confirmed by ELISA using the antigen antibody response as explained in Section E of Example 1.

The *Lb. Plantarum* in which the expression of cholera flagellin protein was confirmed was used to prepare a freeze-dried microorganism cell powder as in Section F of Example 1, and a seamless capsule formulation, a soft capsule formulation, and a hard capsule formulation, each of which contains the freeze-dried microorganism cell powders, were prepared respectively as in Sections G, H, and I of Example 1. The membranes of the resultant seamless capsule formulation, soft capsule formulation, and hard capsule formulation were acid resistant.

Example 3

Preparation of Acid-Resistant Capsule Formulation Containing Bifidobacteria Producing Dysentery Antigen

*S. dysenteriae* ATCC 29026, which produces a dysentery antigen, was cultured in LB medium at 37° C. for 12 hours. After completion of the culture, the genomic DNA was conventionally extracted from *S. dysenteriae*. PCR was performed as in Example 1, using the extracted genomic DNA as a template with the sequences of SEQ ID NO: 5 (forward) and SEQ ID NO: 6 (reverse) as a pair of primers. The resultant amplified fragment was recovered and cleaved with NcoI and BamHI. Thus, the fragment for dysentery flagellin gene was prepared. The pBLES-FliC prepared in Example 1 was digested with NcoI and BamHI, and a large fragment was recovered. This fragment and the dysentery flagellin gene fragment were ligated to each other. Thus, a dysentery antigen-expressing expression vector pBLES-Sd was obtained.

The obtained dysentery flagellin expression vector pBLES-Sd was used to transform *B. longum* ATCC 15697 to prepare *B. longum* producing a dysentery antigen. The expression of the dysentery antigen was confirmed by ELISA using the antigen antibody response as explained in Section E of Example 1.

*B. longum* in which the expression of dysentery flagellin protein was confirmed was used to prepare freeze-dried microorganism cell powders as in Section F of Example 1, and a seamless capsule formulation, a soft capsule formulation, and a hard capsule formulation, each of which contains the freeze-dried microorganism cell powders, were prepared respectively as in Sections G, H, and I of Example 1. The membranes of the obtained seamless capsule formulation, soft capsule formulation, and hard capsule formulation were acid resistant.

Comparative Example 1

A seamless capsule formulation was prepared as in Example 1, except that the gelatin solution for the membrane of Section G of Example 1 was changed to a material obtained by dissolving 600 g of gelatin, 300 g of glycerin, and 100 g of sorbitol in 4 kg of purified water. The membrane of the obtained pharmaceutical was not acid resistant.

Comparative Example 2

A soft capsule formulation was prepared as in Example 1, except that coating of Section H of Example 1 was not performed in the preparation of the soft capsule. The membrane of the obtained pharmaceutical was not acid resistant.

Comparative Example 3

A hard capsule formulation was prepared as in Example 1, except that coating of Section I of Example 1 was not performed in the preparation of the hard capsule. The membrane of the obtained pharmaceutical was not acid resistant.

Comparative Examples 4 to 6

In Comparative Examples 4 to 6, a seamless capsule formulation, a soft capsule formulation, and a hard capsule formulation were prepared respectively as explained in Comparative Examples 1 to 3, except that the microorganism was changed to the cholera flagellin-expressing transformed microorganism prepared as explained in Example 2. The membranes of the obtained seamless capsule formulation, soft capsule formulation, and hard capsule formulation were not acid resistant.

Comparative Examples 7 to 9

In Comparative Examples 7 to 9, a seamless capsule formulation, a soft capsule formulation, and a hard capsule formulation were prepared respectively as explained in Comparative Examples 1 to 3, except that the microorganism was changed to the dysentery *bacillus* flagellin-expressing transformed microorganism prepared as explained in Example 3. The membranes of the obtained seamless capsule formulation, soft capsule formulation, and hard capsule formulation were not acid resistant.

Example 4

Examination for the Antibody Induction Resulting from Administration of Typhoid Fever Flagellin Protein-Expressing Transformed Microorganism (Recombinant *B. animalis*)

First, 8 to 12 week old BALB/c female mice (provided by Charles River Laboratories Japan, Inc.) were purchased, and adapted for one week with a standard diet. The mice were divided into nine groups (5 to 7 mice per group). For three groups, the seamless capsule formulation, the soft capsule formulation, and the hard capsule formulation, which were prepared in Example 1, were orally administered separately, each of which contained the typhoid fever flagellin-expressing transformed microorganism. For another three groups, the non-acid-resistant seamless capsule formulation, soft capsule formulation, and hard capsule formulation, which were prepared in Comparative Examples 1 to 3, respectively, were orally administered separately, each of which contained the typhoid fever flagellin-expressing transformed microorganism. For yet another three groups, flagellin-expressing transformed microorganism (recombinant *B. animalis*) live cells, host *B. animalis* live cells, and a phosphate buffer were administered separately, as controls. These capsule formulations, live cells, and the like were ingested once a day for three weeks.

After three weeks, the amounts of IgA in serum and stools were measured as follows. PBS containing flagellin antigen was added to a 96-well plate (Nunc Immunoplate Maxisorb F96, manufactured by Nalge Nunc International K.K.), and was kept at 4° C. for 16 hours for coating the surface of the plate. Subsequently, PBS containing 1 w/v % of bovine serum albumin was used for blocking at room temperature for 2 hours. After washing with PBS three times, a serum or stool sample was added and reacted at room temperature for three hours. After washing with PBS three times, a secondary antibody (goat-derived-anti-mouse IgA, IgG, IgM (manufactured by Santa Cruz Biotechnology, Inc) was added, and incubated at room temperature for three hours. After washing with PBS three times, a tertiary antibody (fluorescein isothiocyanate (FITC) labeled rabbit-derived-anti-goat IgG (manufactured by QED Bioscience, Inc.) was added, and incubated at room temperature for three hours. The fluorescence was measured using FluoroscanII (manufactured by Dainippon Sumitomo Pharma Co., Ltd.). Table 1 shows the resultant fluorescence values.

TABLE 1

| Administration sample | Number of BALB/c | Daily dosage $10^7$ cfu/day | IgA in stool (OD ± Std. Error) | IgA in serum (OD ± Std. Error) |
|---|---|---|---|---|
| Example 1: Seam less capsule | 7 | 2.5 | 0.16 ± 0.012 | 0.40 ± 0.145 |
| Example 1: Soft capsule | 7 | 3.2 | 0.15 ± 0.013 | 0.38 ± 0.151 |
| Example 1: Hard capsule | 7 | 3 | 0.14 ± 0.014 | 0.37 ± 0.120 |
| Comparative Example 1: Seam less capsule | 5 | 2.5 | 0.05 ± 0.011 | 0.12 ± 0.038 |
| Comparative Example 2: Soft capsule | 5 | 3.2 | 0.06 ± 0.010 | 0.14 ± 0.041 |
| Comparative Example 3: Hard capsule | 5 | 3 | 0.06 ± 0.010 | 0.13 ± 0.028 |
| Transformed microorganism live cells | 5 | 2.5 | 0.04 ± 0.012 | 0.11 ± 0.041 |
| Host microorganism live cells | 5 | 12 | 0.02 ± 0.008 | 0.10 ± 0.038 |
| Phosphate buffer | 5 | — | 0.02 ± 0.006 | 0.14 ± 0.032 |

It was seen that, in the cases of the acid-resistant seamless capsule, soft capsule, and hard capsule formulations prepared in Example 1, regardless of the form of the acid-resistant capsule formulation, the amounts of IgA were larger in both stools and blood and the effect of inducing an antibody was higher, compared with the cases of the non-acid-resistant capsule formulations of the Comparative Examples 1 to 3 or the live cells.

Example 5

Examination for the Antibody Induction Resulting from Administration of Cholera Flagellin-Expressing Transformed Microorganism The seamless capsule formulation, the soft capsule formulation, and the hard capsule formulation, which were prepared in Example 2, and the capsule formulations of Comparative Examples 4 to 6 were examined for the antibody induction as in Example 4, each of which contained the cholera flagellin-expressing transformed microorganism (recombinant *Lb. plantarum*) cells.

Furthermore, cholera flagellin-expressing transformed microorganism live cells, host Lb. plantarum live cells, and a phosphate buffer were used for control administrations. Table 2 shows the results.

TABLE 2

| Administration sample | Number of BALB/c | Daily dosage $10^7$ cfu/day | IgA in stool (OD ± Std. Error) | IgA in serum (OD ± Std. Error) |
|---|---|---|---|---|
| Example 2: Seam less capsule | 7 | 2.8 | 0.15 ± 0.012 | 0.42 ± 0.133 |
| Example 2: Soft capsule | 7 | 3.3 | 0.13 ± 0.013 | 0.41 ± 0.142 |
| Example 2: Hard capsule | 7 | 3.2 | 0.13 ± 0.014 | 0.39 ± 0.140 |
| Comparative Example 4: Seam less capsule | 5 | 2.8 | 0.05 ± 0.011 | 0.13 ± 0.038 |
| Comparative Example 5: Soft capsule | 5 | 3.3 | 0.06 ± 0.010 | 0.12 ± 0.052 |
| Comparative Example 6: Hard capsule | 5 | 3.2 | 0.06 ± 0.010 | 0.11 ± 0.028 |
| Transformed microorganism live cells | 5 | 2.8 | 0.03 ± 0.012 | 0.12 ± 0.032 |
| Host microorganism live cells | 5 | 8.3 | 0.02 ± 0.008 | 0.10 ± 0.022 |
| Phosphate buffer | 5 | — | 0.02 ± 0.006 | 0.15 ± 0.033 |

It was seen that, in the cases of the acid-resistant seamless capsule, soft capsule, and hard capsule formulations prepared in Example 2, regardless of the form of the acid-resistant capsule formulation, the amounts of IgA were larger in both stools and blood and the effect of inducing an antibody was higher, compared with the cases of the non-acid-resistant capsule formulations of the Comparative Examples 4 to 6 or the live cells.

Example 6

Examination for the Antibody Induction Resulting from Administration of Dysentery Flagellin-Expressing Transformed Microorganism The seamless capsule formulation, the soft capsule formulation, and the hard capsule formulation, which were prepared in Example 3, and the capsule formulations of Comparative Examples 7 to 9 were examined for the antibody induction as in Example 4, each of which contained the dysentery bacillus flagellin-expressing transformed microorganism (recombinant B. longum) cells.

Furthermore, dysentery flagellin-expressing transformed microorganism live cells, host B. longum live cells, and a phosphate buffer were used for control administrations. Table 3 shows the results.

TABLE 3

| Administration sample | Number of BALB/c | Daily dosage $10^7$ cfu/day | IgA in stool (OD ± Std. Error) | IgA in serum (OD ± Std. Error) |
|---|---|---|---|---|
| Example 3: Seam less capsule | 7 | 3.2 | 0.13 ± 0.012 | 0.38 ± 0.142 |
| Example 3: Soft capsule | 7 | 3.9 | 0.12 ± 0.013 | 0.37 ± 0.153 |
| Example 3: Hard capsule | 7 | 4 | 0.13 ± 0.014 | 0.39 ± 0.131 |
| Comparative Example 7: Seam less capsule | 5 | 3.2 | 0.06 ± 0.011 | 0.11 ± 0.038 |
| Comparative Example 8: Soft capsule | 5 | 3.9 | 0.05 ± 0.010 | 0.12 ± 0.051 |
| Comparative Example 9: Hard capsule | 5 | 4 | 0.06 ± 0.010 | 0.11 ± 0.028 |
| Transformed microorganism live cells | 5 | 3.2 | 0.02 ± 0.012 | 0.11 ± 0.038 |
| Host microorganism live cells | 5 | 10.1 | 0.03 ± 0.008 | 0.13 ± 0.036 |
| Phosphate buffer | 5 | — | 0.03 ± 0.006 | 0.14 ± 0.031 |

It was seen that, in the cases of the acid-resistant seamless capsule, soft capsule, and hard capsule formulations prepared in Example 3, regardless of the form of the acid-resistant capsule formulation, the amounts of IgA were larger in both stools and blood and the effect of inducing an antibody was higher, compared with the cases of the non-acid-resistant capsule formulations of the Comparative Examples 7 to 9 or the live cells.

Example 7

Preparation of Acid-Resistant Capsule formulation Containing Bifidobacteria that Secrete Typhoid Fever Antigen Out of the Cell of the Microorganism A. Amplification of S. Typhimurium Flagellin Gene through PCR The fragment for S. typhimurium flagellin gene was prepared as in Section A of Example 1.

B. Amplification of Secretion Signal Peptide DNA through PCR

B. bifidum ATCC 29521 was cultured in MRS medium (manufactured by Nippon Becton Dickinson Company, Ltd.) at 37° C. for 12 hours. After completion of the culture, the genomic DNA (Access #AJ224435) of B. bifidum was conventionally extracted. PCR was performed as in Section A of Example 1, using the genomic DNA of B. bifidum as a template with a pair of primers of SEQ ID NO: 11 (forward): 5'-CGGCAAGCTTTATGGGGGATACAGGATTGGCGAT-3' (AAGCTT at positions 5 to 10 is the HindIII cleavage site) and SEQ ID NO: 12 (reverse): 5'-GCGCCCATG-GAAATCGGGTGGCGTCCTCGACCG-3' (CCATGG at positions 5 to 10 is the NcoI cleavage site). After completion of PCR, the resultant was cleaved with HindIII and NcoI. Thus, the fragment for secretion signal peptide gene was prepared.

C. Preparation of Secretion-Type Expression Vector

The plasmid pBLES100 was cleaved with BamHI and HindIII, and combined with and ligated to the flagellin gene fragment obtained in Section A described above and the secretion signal peptide gene fragment obtained in Section B described above. Thus, a secretion-type expression vector pBLES-SP-FliC was obtained.

D. Introduction of Secretion-Type Expression Vector into B. breve

The transformation was performed as in Section D of Example 1, except that pBLES-SP-FliC obtained in Section C described above was used as the expression vector, and B. breve ATCC 15700 was used as the microorganism to be transformed. Thus, transformed B. breve was obtained.

E. Confirmation of Secretion

The transformed *B. breve* obtained in Section D described above was cultured in marble-containing MRS broth medium at 37° C. for 12 hours, and subsequently, centrifuged at 4° C. and 12000 rpm, and the supernatant was obtained. The supernatant was subjected to Western blotting as in Section E of Example 1. It was confirmed that a flagellin protein was secreted out of the cells of transformed *B. breve*.

F. Preparation of a Freeze-Dried Microorganism Powder of the Transformed Microorganism The *B. breve* confirmed for secretion of typhoid fever flagellin was confirmed was used to prepare freeze-dried microorganism cell powders as in Section F of Example 1.

G. Preparation of Acid-Resistant Seamless Capsule Formulation, Soft Capsule formulation, and Hard Capsule formulation With the freeze-dried microorganism powders obtained as explained in Section F described above, a seamless capsule formulation, a soft capsule formulation, and a hard capsule formulation were prepared as in Sections G, H, and I of Example 1, respectively. The membranes of the obtained seamless capsule formulation, soft capsule formulation, and hard capsule formulation were acid resistant.

Comparative Examples 10 to 12

In Comparative Examples 10 to 12, a seamless capsule formulation, a soft capsule formulation, and a hard capsule formulation were prepared respectively as in Comparative Examples 1 to 3, except that the microorganism was changed to the typhoid fever flagellin-secretory expressing transformed microorganism prepared as in Example 7. The membranes of the obtained seamless capsule formulation, soft capsule formulation, and hard capsule formulation were not acid resistant.

Example 8

The seamless capsule formulation, the soft capsule formulation, and the hard capsule formulation, which were obtained in Example 7, and the capsule formulations of Comparative Examples 10 to 12 were examined for the antibody induction as in Example 4, each of which contained the typhoid fever flagellin-secretory expressing transformed microorganism (recombinant *B. breve*) cells.

Furthermore, typhoid fever flagellin-secretory expressing transformed microorganism (recombinant *B. breve*) live cells, host *B. breve* live cells, and a phosphate buffer were used for control administrations. Table 4 shows the results.

TABLE 4

| Administration sample | Number of BALB/c | Daily dosage $10^7$ cfu/day | IgA in stool (OD ± Std. Error) | IgA in serum (OD ± Std. Error) |
|---|---|---|---|---|
| Example 7: Seam less capsule | 7 | 3.5 | 0.18 ± 0.015 | 0.44 ± 0.155 |
| Example 7: Soft capsule | 7 | 4.1 | 0.16 ± 0.013 | 0.42 ± 0.148 |
| Example 7: Hard capsule | 7 | 3.6 | 0.20 ± 0.014 | 0.38 ± 0.140 |
| Comparative Example 10: Seam less capsule | 5 | 3.5 | 0.05 ± 0.012 | 0.12 ± 0.033 |
| Comparative Example 11: Soft capsule | 5 | 4.1 | 0.04 ± 0.011 | 0.11 ± 0.046 |
| Comparative Example 12: Hard capsule | 5 | 3.6 | 0.06 ± 0.013 | 0.14 ± 0.034 |
| Transformed microorganism live cells | 5 | 3.4 | 0.05 ± 0.011 | 0.13 ± 0.036 |
| Host microorganism live cells | 5 | 10.5 | 0.03 ± 0.009 | 0.12 ± 0.039 |
| Phosphate buffer | 5 | — | 0.02 ± 0.007 | 0.13 ± 0.040 |

It was seen that, in the cases of the acid-resistant seamless capsule, soft capsule, and hard capsule formulations containing the typhoid fever flagellin-secretory expressing transformed microorganism prepared in Example 7, regardless of the form of the acid-resistant capsule formulation, the amounts of IgA were larger in both stools and blood and the effect of inducing an antibody was higher, compared with the cases of the non-acid-resistant capsule formulations of the Comparative Examples 10 to 12 or the live cells.

INDUSTRIAL APPLICABILITY

A formulation in which a transformed microorganism that expresses flagellin is contained in an acid-resistant capsule increases the amount of anti-flagellin antibody produced, and thus is effective as an oral vaccine against a bacterial infectious disease, such as typhoid fever, cholera, or dysentery. Therefore, a method for preventing and treating bacterial infectious diseases can be provided. In consideration of recent prevalent drug-resistant infectious pathogenic bacteria, the administration of such an oral vaccine to people living in an endemic area or people visiting such an area on business or on holiday is an ideal strategy for prevention and treatment.

The invention claimed is:

1. An oral vaccine against a bacterial infectious disease, in the form of a capsule formulation, comprising: a capsule membrane and a transformed microorganism that expresses a flagellin antigen protein, wherein the capsule membrane is acid resistant, and the transformed microorganism is encapsulated with the capsule membrane, wherein the microorganism is at least one selected from microorganisms belonging to the group consisting of the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella*.

2. The oral vaccine of claim 1, wherein the flagellin antigen protein is expressed in the cell of the microorganism.

3. The oral vaccine of claim 1, wherein the flagellin antigen protein is secreted out of the cell of the microorganism.

4. The oral vaccine of claim 1, wherein the oral vaccine is a vaccine against typhoid fever, cholera, or dysentery.

5. The oral vaccine of claim 1, wherein the capsule formulation is a seamless capsule formulation, a soft capsule formulation, or a hard capsule formulation.

6. An oral vaccine against a bacterial infectious disease, in the form of a capsule formulation, comprising:
 a capsule membrane and
 a transformed microorganism that expresses a flagellin antigen protein,
 wherein the capsule membrane is acid resistant, and the transformed microorganism is encapsulated with the capsule membrane,
 wherein the microorganism is at least one selected from microorganisms belonging to the group consisting of the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella*, and
 wherein the oral vaccine is a vaccine against typhoid fever, cholera, or dysentery.

7. The oral vaccine of claim 6 wherein the microorganisms belong to the genus *Bifidobacterium*.

8. The oral vaccine of claim 6, wherein the capsule formulation is a seamless capsule formulation, a soft capsule formulation, or a hard capsule formulation.

9. A method for producing an oral vaccine against a bacterial infectious disease, comprising the steps of: preparing a transformed microorganism that expresses a flagellin antigen protein; and enveloping the transformed microorganism in an acid-resistant capsule membrane, thereby producing an acid-resistant capsule formulation, wherein the microorganism is at least one selected from microorganisms belonging to the group consisting of the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella*.

10. The method of claim 9, wherein the transformed microorganism expresses the flagellin antigen protein in the cell of the microorganism.

11. The method of claim 9, wherein the transformed microorganism secretes the flagellin antigen protein out of the cell of the microorganism.

12. The method of claim 9, wherein the oral vaccine is a vaccine against typhoid fever, cholera, or dysentery.

13. The method of claim 9, wherein the capsule formulation is a seamless capsule formulation, a soft capsule formulation, or a hard capsule formulation.

14. A method for producing an oral vaccine against a bacterial infectious disease, comprising the steps of: preparing a transformed microorganism that expresses a flagellin antigen protein; enveloping the transformed microorganism in a capsule membrane, thereby producing a capsule formulation; and providing the capsule membrane of the produced capsule formulation with acid resistance, wherein the microorganism is at least one selected from microorganisms belonging to the group consisting of the genus *Bifidobacterium*, the genus *Lactobacillus*, the genus *Lactococcus*, the genus *Pediococcus*, the genus *Streptococcus*, the genus *Enterococcus*, the genus *Leuconostoc*, the genus *Tetragenococcus*, the genus *Oenococcus*, and the genus *Weissella*.

15. The method of claim 14, wherein the transformed microorganism expresses the flagellin antigen protein in the cell of the microorganism.

16. The method of claim 14, wherein the transformed microorganism secretes the flagellin antigen protein out of the cell of the microorganism.

17. The method of claim 14, wherein the oral vaccine is a vaccine against typhoid fever, cholera, or dysentery.

18. The method of claim 14, wherein the capsule formulation is a seamless capsule formulation, a soft capsule formulation, or a hard capsule formulation.

* * * * *

SEQUENCE LISTING

```
<160> NUMBER OF SEQ ID NOS: 12

<210> SEQ ID NO 1
<211> LENGTH: 30
<212> TYPE: DNA
<213> ORGANISM: Artificial
<220> FEATURE:
<223> OTHER INFORMATION: Salmonella typhimurium forward primer

<400> SEQUENCE: 1
catgccatgg atggcacagt cattaataca                                    30

<210> SEQ ID NO 2
<211> LENGTH: 30
```

-continued

```
<212> TYPE: DNA
<213> ORGANISM: Artificial
<220> FEATURE:
<223> OTHER INFORMATION: Salmonella typhimurium reverse primer

<400> SEQUENCE: 2
cgcggatcct taacgcagta aagagaggac                                  30

<210> SEQ ID NO 3
<211> LENGTH: 31
<212> TYPE: DNA
<213> ORGANISM: Artificial
<220> FEATURE:
<223> OTHER INFORMATION: Vibrio cholerae forward primer

<400> SEQUENCE: 3
catgccatgg atggcaatta atgtaaacac g                                31

<210> SEQ ID NO 4
<211> LENGTH: 31
<212> TYPE: DNA
<213> ORGANISM: Artificial
<220> FEATURE:
<223> OTHER INFORMATION: Vibrio cholerae reverse primer

<400> SEQUENCE: 4
cgcggatcct ttatcccaat aagctcagag c                                31

<210> SEQ ID NO 5
<211> LENGTH: 30
<212> TYPE: DNA
<213> ORGANISM: Artificial
<220> FEATURE:
<223> OTHER INFORMATION: Shigella dysenteriae forward primer

<400> SEQUENCE: 5
catgccatgg atggcacaag tcattaatac                                  30

<210> SEQ ID NO 6
<211> LENGTH: 30
<212> TYPE: DNA
<213> ORGANISM: Artificial
<220> FEATURE:
<223> OTHER INFORMATION: Shigella dysenteriae reverse primer

<400> SEQUENCE: 6
cgcggatcct ttaaccctgc tgcagagaca                                  30

<210> SEQ ID NO 7
<211> LENGTH: 30
<212> TYPE: DNA
<213> ORGANISM: Artificial
<220> FEATURE:
<223> OTHER INFORMATION: hup forward primer

<400> SEQUENCE: 7
cgccaagctt tgggcgcggc ggccatgaag                                  30

<210> SEQ ID NO 8
<211> LENGTH: 30
<212> TYPE: DNA
<213> ORGANISM: Artificial
<220> FEATURE:
<223> OTHER INFORMATION: hup reverse primer

<400> SEQUENCE: 8
```

```
cgcgccatgg aaagcatcct tcttgggtca                               30
```

```
<210> SEQ ID NO 9
<211> LENGTH: 600
<212> TYPE: DNA
<213> ORGANISM: Bifidobacterium longum
<220> FEATURE:
<221> NAME/KEY: promoter
<222> LOCATION: (1)..(192)
<220> FEATURE:
<221> NAME/KEY: CDS
<222> LOCATION: (193)..(474)
<220> FEATURE:
<221> NAME/KEY: terminator
<222> LOCATION: (475)..(600)

<400> SEQUENCE: 9
```

```
tgggcgcggc ggccatgaag tggcttgaca agcataatct tgtctgattc gtctattttc    60
atacccccct cggggaaata gatgtgaaaa cccttataaa acgcgggttt tcgcagaaac   120
atgcgctagt atcattgatg acaacatgga ctaagcaaaa gtgcttgtcc cctgacccaa   180
gaaggatgct tt atg gca tac aac aag tct gac ctc gtt tcg aag atc gcc   231
              Met Ala Tyr Asn Lys Ser Asp Leu Val Ser Lys Ile Ala
              1               5                  10 cag aag tcc aac ctg acc aag gct cag gcc gag gct gct gtt aac gcc    279
Gln Lys Ser Asn Leu Thr Lys Ala Gln Ala Glu Ala Ala Val Asn Ala
        15                  20                  25 ttc cag gat gtg ttc gtc gag gct atg aag tcc ggc gaa ggc ctg aag    327
Phe Gln Asp Val Phe Val Glu Ala Met Lys Ser Gly Glu Gly Leu Lys
30                  35                  40                  45 ctc acc ggc ctg ttc tcc gct gag cgc gtc aag cgc ccg gct cgc acc    375
Leu Thr Gly Leu Phe Ser Ala Glu Arg Val Lys Arg Pro Ala Arg Thr
                50                  55                  60 ggc cgc aac ccg cgc act ggc gag cag att gac att ccg gct tcc tac    423
Gly Arg Asn Pro Arg Thr Gly Glu Gln Ile Asp Ile Pro Ala Ser Tyr
            65                  70                  75 ggc gtt cgt atc tcc gct ggc tcc ctg ctg aag aag gcc gtc acc gag    471
Gly Val Arg Ile Ser Ala Gly Ser Leu Leu Lys Lys Ala Val Thr Glu
        80                  85                  90 tga ccttctgctc gtagcgatta cttcgagcat tactgacgac aaagaccccg          524
accgagatgg tcgggggtctt tttgttgtgg tgctgtgacg tgttgtccaa ccgtattatt   584
ccggactagt tcagcg                                                    600
```

```
<210> SEQ ID NO 10
<211> LENGTH: 93
<212> TYPE: PRT
<213> ORGANISM: Bifidobacterium longum

<400> SEQUENCE: 10
```

```
Met Ala Tyr Asn Lys Ser Asp Leu Val Ser Lys Ile Ala Gln Lys Ser
1               5                   10                  15

Asn Leu Thr Lys Ala Gln Ala Glu Ala Ala Val Asn Ala Phe Gln Asp
            20                  25                  30

Val Phe Val Glu Ala Met Lys Ser Gly Glu Gly Leu Lys Leu Thr Gly
        35                  40                  45

Leu Phe Ser Ala Glu Arg Val Lys Arg Pro Ala Arg Thr Gly Arg Asn
    50                  55                  60

Pro Arg Thr Gly Glu Gln Ile Asp Ile Pro Ala Ser Tyr Gly Val Arg
65                  70                  75                  80

Ile Ser Ala Gly Ser Leu Leu Lys Lys Ala Val Thr Glu
            85                  90
```

-continued

```
<210> SEQ ID NO 11
<211> LENGTH: 34
<212> TYPE: DNA
<213> ORGANISM: Artificial
<220> FEATURE:
<223> OTHER INFORMATION: Bifidobacterium bifidum forward primer

<400> SEQUENCE: 11
cggcaagctt tatgggggat acaggattgg cgat                             34

<210> SEQ ID NO 12
<211> LENGTH: 33
<212> TYPE: DNA
<213> ORGANISM: Artificial
<220> FEATURE:
<223> OTHER INFORMATION: Bifidobacterium bifidum reverse primer

<400> SEQUENCE: 12
gcgcccatgg aaatcgggtg gcgtcctcga ccg                              33
```